(12) United States Patent
Kablotsky

(10) Patent No.: US 7,679,751 B1
(45) Date of Patent: Mar. 16, 2010

(54) METHOD AND APPARATUS FOR THREE-DIMENSIONAL IMAGING

(75) Inventor: Joshua A. Kablotsky, Carlisle, MA (US)

(73) Assignee: Analog Devices, Inc., Norwood, MA (US)

( * ) Notice: Subject to any disclaimer, the term of this patent is extended or adjusted under 35 U.S.C. 154(b) by 0 days.

(21) Appl. No.: 12/276,531

(22) Filed: Nov. 24, 2008

(51) Int. Cl.
*G01N 21/55* (2006.01)

(52) U.S. Cl. ...................................... 356/445; 356/447

(58) Field of Classification Search ................. 356/445, 356/447
See application file for complete search history.

(56) References Cited

U.S. PATENT DOCUMENTS 5,031,154 A * 7/1991 Watanabe .................. 367/8

* cited by examiner

*Primary Examiner*—Roy Punnoose
(74) *Attorney, Agent, or Firm*—Goodwin Procter LLP

(57) ABSTRACT

A method and apparatus are provided for imaging three-dimensional scenes and objects by detecting reflections from emitted sequences of electromagnetic radiation. At least one transmitter is provided for emitting a sequence of electromagnetic radiation, and at least three sensors are provided for detecting radiation reflected from the scene and objects being imaged. Signals based on the detected radiation are used, together with spatial information of the transmitters and sensors, to calculate reflectivity coefficients for points of interest in the scene. Velocity vectors associated with moving objects within the scene can also be determined based on the rate of change of the phase differences between the emitted and reflected radiations.

14 Claims, 2 Drawing Sheets

METHOD AND APPARATUS FOR THREE-DIMENSIONAL IMAGING

FIELD OF THE INVENTION

The present invention relates to a method and apparatus for imaging three-dimensional scenes by detecting reflections from emitted sequences of electromagnetic radiation. Velocity vectors associated with objects within a scene being imaged can also be determined.

BACKGROUND

There are several techniques for identifying the distance, location or speed of moving and fixed objects. One such technique is radar, which uses radio waves provided by a transmitter, and detects reflected waves to determine the location or speed of an object located some distance from the transmitter.

Laser-based techniques can also be used to provide such information. For example, LADAR (Laser Detection and Ranging) and LIDAR (Light Detection and Ranging) direct electromagnetic waves toward an object from a source (e.g., a light source or laser). The object reflects a portion of the waves, and the reflected waves are detected by one or more sensors, such as photodetectors.

Such techniques can be used to determine the distance between the source and the object based on the round-trip travel time from the source to the object and back to the sensors. The velocity of moving objects can also be estimated using such systems based on, e.g., the rate of change of the phase differences between the transmitted waves and the reflected waves.

The imaging of distant objects and scenes can also be performed using such techniques. However, such systems generally use an array of detectors, and the resolution is often limited by the size of the array, e.g., the number of detectors or pixels in the sensor array.

Accordingly, there is a demand for imaging methods and systems which can provide imaging of objects and scenes using a small number of detectors or transmitters, for which the achievable spatial resolution is not limited by the number of detectors or bandwidth of the system.

SUMMARY OF THE INVENTION

An apparatus and method are provided for three-dimensional imaging of objects and scenes. In one aspect of the invention, a system is provided which includes at least one transmitter, e.g., a diffused laser or a light-emitting diode ("LED"), and three or more sensors, e.g., detectors such as photodetectors, where at least one sensor is not co-linear with two other sensors. The transmitter is configured to emit a sequence of electromagnetic radiation, such as a modulated continuous wave or a series of pulses, toward the scene and the objects to be imaged. The sensors are configured to detect reflected radiation.

The system further includes a processing arrangement which is configured to process signals from the sensors based on the reflected radiation. The processing arrangement is further configured to estimate reflective coefficients at a plurality of spatial locations associated with the scene and objects being imaged. These reflectivities are determined based on a mathematical analysis of the signals from the sensors, including a comparison of these signals to expected signals based on path delays between the transmitter, the spatial locations, and each sensor. The scene and objects can then be imaged in three dimensions based on the calculated reflectivities.

In a further aspect of the invention, a system is provided which includes at least three transmitters and at least one sensor, where at least one transmitter is not co-linear with the other transmitters. The transmitters are configured to emit sequences of electromagnetic radiation, such as modulated continuous waves, toward the scene and objects to be imaged. The sensor is configured to detect reflected radiation.

The system further includes a processing arrangement which is configured to process signals from the sensor based on the reflected radiation, and to estimate reflective coefficients at a plurality of spatial locations associated with the scene and objects being imaged. The reflectivities are determined based on a mathematical analysis of the signals from the sensors, including a comparison of these signals to expected signals based on path delays between the transmitters, the spatial locations, and the sensor. The scene and objects can then be imaged in three dimensions based on the calculated reflectivities.

In certain embodiments, the processing arrangement is further configured to calculate 3-dimensional motion vectors associated with an object within that scene based on the rate of change of the phase differences between the radiation emitted by the transmitter and the reflected radiation signals received by the sensors.

In a further aspect, a method is provided for imaging a scene and objects in three dimensions. A sequence of electromagnetic radiation, e.g., a series of pulses or a modulated continuous wave, is emitted by at least one transmitter (e.g., an LED or a diffused laser) towards the scene and objects. Reflections of the radiation from the scene and objects are detected by at least three sensors, where at least one sensor is not co-linear with the other sensors. In certain embodiments, the sequence is emitted by at least three transmitters, where at least one transmitter is not co-linear with the other transmitters, and reflections of radiation from the scene or objects are detected by one or more sensors.

For each sensor, expected amplitudes of reflected signals can be calculated at various delays for the sequence transmitted from each transmitter. A round-trip delay is calculated for the path from each of the transmitters to each point of interest in three-dimensional space and back to each of the sensors. A reflectivity at each point of interest is then calculated based on the expected amplitudes, the round-trip delays, and the actual amplitudes of reflected radiation detected by each sensor.

In certain embodiments, the estimated reflectivity at a point of interest is modified to account for line-of-sight obstructions which may occur between a transmitter or a sensor and the point of interest. In further embodiments, the estimation of reflectivities is augmented to account for second-order reflections.

In further embodiments, three-dimensional vectors associated with the velocity of an object within that scene are calculated based on the rate of change of the phase differences corresponding to frequency shifts (e.g., Doppler shifts) between the radiation emitted by the transmitters and the reflected radiation signals received by the sensors. Such shifts at each point of interest can be used to obtain velocity information, and this information is then combined for three or more transmitter/sensor pairs to obtain a three-dimensional velocity vector associated with the point of interest.

BRIEF DESCRIPTION OF THE DRAWINGS

The foregoing and other objects, aspects, features, and advantages of the invention will become more apparent and may be better understood by referring to the following description taken in conjunction with the accompanying drawings, in which.

Figure 1:
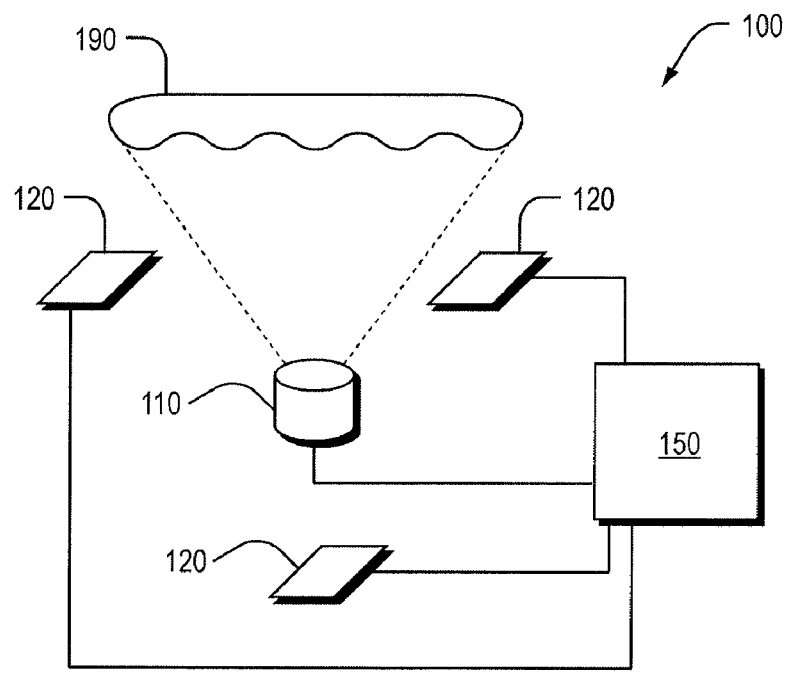
FIG. 1 is a schematic illustration of a system which can be used to image scenes and objects in three dimensions.

Throughout the drawings, the same reference numerals and characters, unless otherwise stated, are used to denote like features, elements, components, or portions of the illustrated embodiments. Moreover, while the present invention will now be described in detail with reference to the figures, it is done so in connection with the illustrative embodiments and is not limited by the particular embodiments shown in the figures.

DETAILED DESCRIPTION

An exemplary system 100 for three-dimensional imaging of objects and scenes is shown in FIG. 1. The system 100 includes at least one transmitter 110 which is configured to direct electromagnetic radiation towards the scene 190, which may include one or more objects. The transmitter 110 may include an LED, a laser source that is diffused or spread such that the radiation is directed toward the entire scene 190 to be imaged, etc.

The transmitter 110 is configured to emit a sequence of electromagnetic radiation such as, e.g., a series of spaced-apart pulses or a continuous wave that is temporally modulated by amplitude or intensity. The sequence can be based on, e.g., a pseudorandom number sequence or another mathematical function such as a phase-modulated Fourier transformed pulse. If a plurality of transmitters 110 are used, each such transmitter 110 preferably emits a distinct sequence of electromagnetic radiation.

The system 110 also includes three or more sensors 120, which are preferably provided at fixed and predetermined locations relative to the transmitter 110. The sensors 120 are configured such that at least one sensor 120 is not co-linear with the others. The sensors 120 are preferably detectors, such as photodetectors, which are configured to detect radiation emitted by the transmitter 110 and reflected from portions of the scene 190 to be imaged. The transmitter 110 is preferably selected such that intensity of electromagnetic radiation emitted therefrom is strong enough to be reflected from the scene 190 and detected by the sensors 120.

The system further includes a processing arrangement 150 which is provided in communication with both the transmitter 110 and the sensors 120. The processing arrangement 150 can include, e.g., a microprocessor, a memory arrangement, and optionally a display device. For example, the processing arrangement 150 may be a personal computer, a workstation, or a customized computing device. The communication between these components is preferably hardwired. In certain embodiments it may be wireless. The processing arrangement 150 receives signals corresponding to the sequence of radiation emitted by the transmitter 110. The processing arrangement 150 may optionally be configured to provide control signals responsible for the sequence of radiation emitted by the transmitter 110. The processing arrangement 150 is configured to process signals received at the sensors 120, which are based on radiation emitted by the transmitter 110 that is reflected from portions of the scene 190.

In one embodiment, the processing arrangement 150 is further configured to calculate the amplitudes of reflected radiation signals expected to be received by the sensors 120 for a plurality of delay times. The delay times represent the delay between the emission of a sequence by a transmitter 110 and the time a reflected portion of that sequence is received by a sensor 120. The delay times used for these calculations may be integer multiples of each other, regular sequences, e.g., geometric or logarithmic sequences, or random sequences.

The expected amplitudes may be calculated in real time during the imaging procedure described herein. In certain embodiments, the expected amplitudes may be calculated in advance, e.g., prior to the imaging procedure, and these amplitudes can be stored together with corresponding delay times in a memory arrangement provided in communication with the processing arrangement 150. These calculated expected amplitudes can be used to reduce errors arising from discrepancies between the predicted received signals and the signals actually received by the sensors 120.

The processing arrangement 150 is configured to calculate round-trip propagation delays associated with each spatial point of interest in the scene 190 being imaged. This round-trip delay represents the time required for a pulse of electromagnetic radiation to travel from the transmitter 110 to the point of interest and back to a sensor 120.

Figure 2:
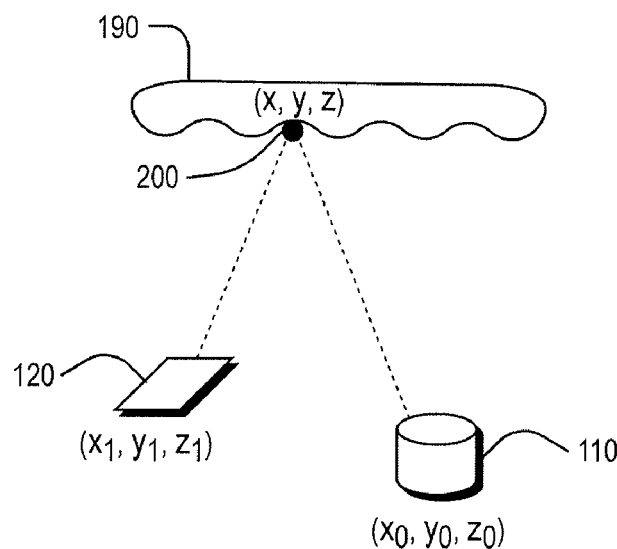
FIG. 2 is a schematic illustration of the geometry which can be used to calculate round-trip delays between a transmitter, a point of interest, and a sensor.

An illustration of the geometry used to calculate these round-trip delays is shown in FIG. 2. A transmitter 110 is located at spatial coordinates $(x_0, y_0, z_0)$ and a sensor 120 is located at spatial coordinates $(x_1, y_1, z_1)$. A point of interest 200 in the scene 190 being imaged, for which a round-trip delay is being calculated, is located at spatial coordinates $(x, y, z)$. The total path length is equal to the sum of the distance from the transmitter 110 to the point 200 and the distance from the point 200 to the sensor 120. These distances can be calculated using the Pythagorean theorem in three dimensions between each pair of coordinates. The round-trip delay is then calculated as this total distance divided by the propagation speed of the electromagnetic radiation, which can be expressed as 'c.' Accordingly, an expression for the round-trip delay associated with the point of interest 200 in FIG. 2 can be written as $[SQRT\{(x_0-x)^2+(y_0-y)^2+(z_0-z)^2\}+SQRT\{(x_1-x)^2+(y_1-y)^2+(z_1-z)^2\}]/c$.

The processing arrangement 150 is further configured to estimate a reflective coefficient associated with each point of interest 200 associated with the scene 190 being imaged. First, for each transmitter 110 and each sensor 120, a partial coefficient associated with the point of interest 200 is determined based on the sequence of radiation emitted by the transmitter 110, the reflected radiation detected by the sensor 120, and the calculated round-trip delay between the transmitter 110, the point of interest 200, and the sensor 120. The expected amplitudes described herein may also be used to improve accuracy, if they are calculated.

Since the received signal may be a combination of noisy echoes, the reflections may be ambiguous. As greater temporal-spatial resolution than that afforded by the sampling rate may be desired, disambiguation may be accomplished by over-defining the system, i.e., by sending and receiving more data points than there are coefficients to be determined, resulting in an optimization problem. Consequently, determination of the partial coefficients can be formulated as a linear optimization problem that may be solved by any one of several conventional techniques, including a least-squares technique, a least-mean squares technique, or the like. The reflective coefficient associated with the point 200 can then be determined based on the partial coefficients calculated for each transmitter/sensor pair. For example, the reflective coefficient associated with the point 200 may be determined by averaging or otherwise combining all of the partial coefficients associated with each transmitter/sensor pair for the point 200.

After the reflective coefficients have been determined, the processing arrangement 150 can be used to generate an image or representation of the scene 190 by presenting each spatial point of interest 200 within the scene 190 according to its corresponding reflectivity. The image or representation can be stored in a memory arrangement or displayed on a monitor or other display device.

The image or representation generated by this process can be refined by accounting for the effects of objects or surfaces in the scene 190 which may obstruct a direct path between a transmitter 110 and the point 200, or a direct path between the point 200 and a sensor 120. For example, a significant difference between a first partial coefficient computed for a first transmitter/sensor pair and a second partial coefficient computed for a second transmitter/sensor pair may indicate the presence of an obstructed path. The effect of such obstruction can be accounted for based on the geometric paths between the point 200 and the transmitter 110 and sensors 120 to improve the accuracy of the image or representation. The generated image or representation may be further augmented by accounting for predicted or estimated second-order reflections based on the initial set of calculated reflection coefficients.

In a further embodiment, motion vectors associated with one or more points 200 in the scene are calculated based on the sequence transmitted by the transmitter 110 and the reflected radiation detected by the sensors 120. The processing arrangement 150 is configured to determine the frequency offset (e.g., Doppler shifts) of the received signals relative to the transmitted sequence at a given delay. This frequency offset, if present, is used to estimate a velocity vector for the point 200 towards or away from the transmitter 110 and a receiver 120. The magnitude of the vector is based on the frequency offset, and the direction is based on the geometric relationship between the transmitter 110, the point 200, and the sensor 120. By combining the velocity vectors estimated for all sensors 120, a three-dimensional motion vector associated with the point 200 may be calculated.

Several techniques may be used to improve the resolution of the generated image or the speed of imaging a scene. For example, a faster sampling rate of signals received from the sensors 120 or increased signal bandwidth used in the transmitters 110 can be used to produce a greater spatial resolution subject to, e.g., Nyquist limits. A greater spatial separation of the transmitter 110 and sensors 120 can also produce a greater spatial resolution, particularly when imaging a scene 190 in the near-field. Undersampling and other numerical signal processing techniques may also be used to achieve greater spatial resolution, but such techniques may increase sensitivity to signal noise, the time needed to gather more samples, or computational requirements of the processing arrangement 150.

Increasing transmitter power or sensor sensitivity (including, e.g., providing signal amplifiers or converters) can increase the effective range of scenes which can be imaged. Using sensors 120 having a larger dynamic range can generate a greater depth of field and greater dynamic range of the resultant image or representation. Also, using a greater number of transmitters 110 or receivers 120 can further reduce the effects of noise on the generation of an image or representation of the scene 190.

For example, transmitters 110 and sensors 120 operating at 100 million samples per second with a 5× interpolation may be used to achieve a spatial imaging resolution of approximately two feet. The sensors 120 can be provided in a triangular configuration around a central transmitter 110, with a separation of approximately four feet between each sensor 120 and the transmitter 110 to achieve such resolution. Other geometric configurations of transmitters and sensors may be used with any of the embodiments described herein. These parameters are exemplary, and other combinations of operating parameters and transmitter/sensor configurations can be provided to achieve a desired resolution for a particular application.

Figure 3:
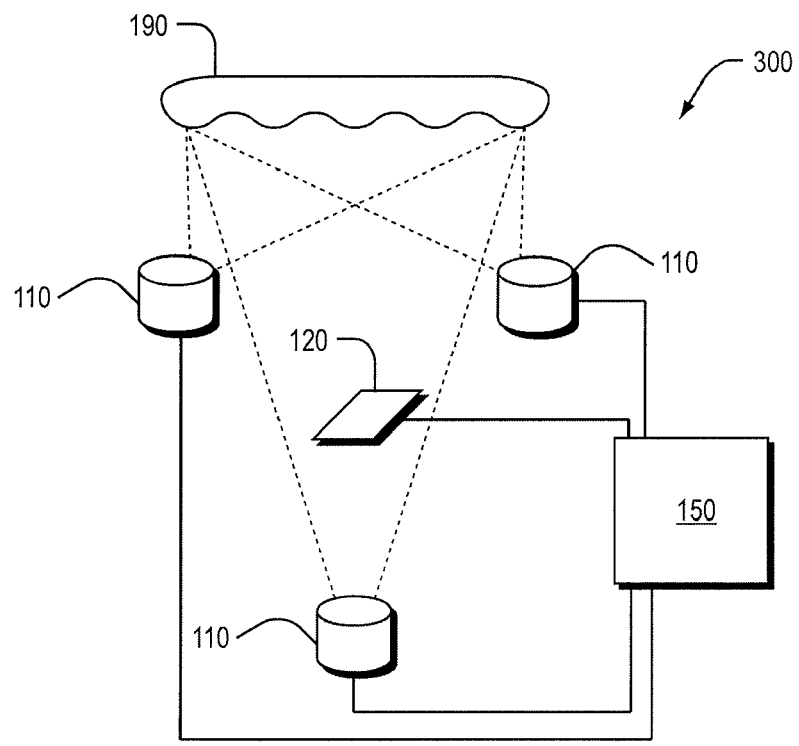
FIG. 3 is a schematic illustration of another system which can be used to image scenes and objects in three dimensions.

In a further aspect, a system 300 for three-dimensional imaging of objects and scenes is provided as shown in FIG. 3. The system 300 includes at least three transmitters 110 and at least one sensor 120. Each transmitter 110 is configured to emit a sequence of electromagnetic radiation as described herein. The transmitters 110 are configured such that at least one transmitter 110 is not co-linear with the others. The sensor 120 and transmitters 110 are preferably provided at fixed and predetermined locations relative to one another.

The system further includes a processing arrangement 150 which is provided in communication with both the transmitters 110 and the sensor 120. The processing arrangement 150 receives signals corresponding to the sequence of radiation emitted by the transmitters 110, and is further configured to receive signals based on radiation emitted by the transmitters 110 that is reflected from portions of the scene 190 and detected by the sensor 120.

The processing arrangement 150 is further configured to generate an image or representation of the scene 190 based on the sequences of radiation emitted by the transmitters 110, the reflected radiation detected by the sensor 120, and the calculated round-trip delay between each transmitter/sensor pair, using techniques similar to those described herein with respect to the system 100 shown in FIG. 1.

In a still further aspect, a system for three-dimensional imaging of objects and scenes is provided which is similar to the systems 100, 300 shown in FIGS. 1 and 3, respectively, that includes at least two transmitters, at least two sensors, and a processing arrangement. Each transmitter is configured to emit a sequence of electromagnetic radiation as described herein. The transmitters and sensors are provided at fixed and predetermined locations relative to one another such that at least one of these components is not co-linear with the others. Generally, a co-linear arrangement of one transmitter and two sensors, or two transmitters and one sensor, can image scenes in a half-plane whose boundary line coincides with the line on which the transmitter(s) and sensor(s) are located. By adding a fourth component, i.e., a second transmitter or sensor, respectively, the capabilities of the system may be extended to three dimensions. Accordingly, a system including at least two transmitters and at least two sensors may be used to generate representations or images of a scene as described herein.

Figure 4:
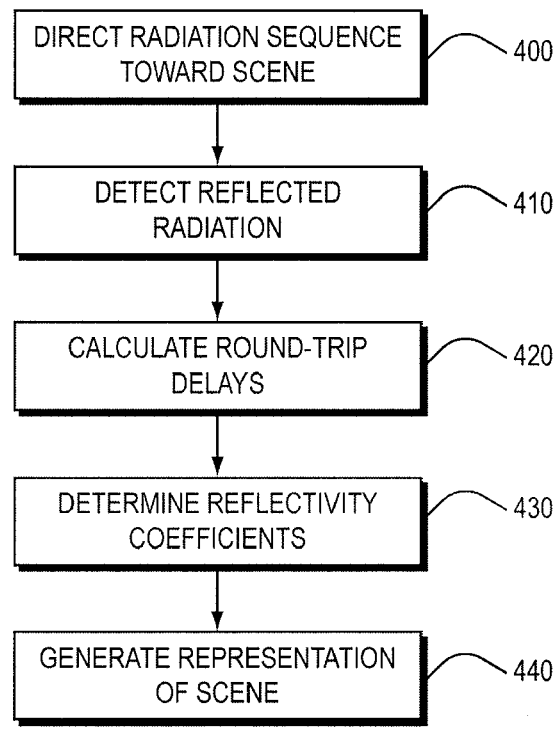
FIG. 4 is a flowchart of a method which may be used to image scenes and objects in three dimensions.

In another aspect, a method is provided for generating a three-dimensional representation of a scene. A flowchart illustrating an embodiment of the method is shown in FIG. 4. A sequence of electromagnetic radiation is directed towards the scene (step 400), which may include one or more objects. The sequence of electromagnetic radiation can be provided by at least one transmitter, such as an LED or a laser source, as described herein. In one embodiment, the sequence is a series of spaced-apart pulses. In a further embodiment, the sequence is a continuous wave that is temporally modulated by amplitude or intensity.

Reflections of the sequence of electromagnetic radiation from the scene are then detected by at least three sensors (step 410), which are preferably provided at fixed and predetermined locations relative to the transmitter. At least one sensor is not co-linear with the others.

A round-trip propagation delay associated with each spatial point of interest in the scene being imaged is then calculated (step 420), as described herein. A reflective coefficient corresponding to each point of interest associated with the scene is then determined based on the sequence of radiation emitted by the transmitter, the reflected radiation detected by the sensors, and the calculated round-trip delays between the transmitter, the point of interest, and each sensor (step 430). The reflective coefficients can be determined based on partial coefficients corresponding to each transmitter/receiver pair as described herein.

Expected amplitudes of reflected radiation to be received by each sensor may be calculated based on the sequence of electromagnetic radiation provided by the transmitter and the round-trip delay between the transmitter, the point of interest, and each sensor. These expected amplitudes may also be used when determining the reflective coefficients (step 430) to improve accuracy of the calculations.

An image or representation of the scene is then generated based on the reflective coefficients determined for the points of interest (step 440). This image or representation may then be stored in a memory arrangement or displayed on a monitor or other display device.

The image or representation can be refined by accounting for secondary reflections or path obstructions between a point of interest and a transmitter or sensor, as described herein.

In a further embodiment, three-dimensional motion vectors associated with one or more points in the scene are calculated based on frequency offsets between the transmitted sequence and the corresponding reflected radiation received at each sensor, as described herein.

In still another embodiment, the sequence of electromagnetic radiation in step 400' is a plurality of distinct sequences provided by at least three spatially separated transmitters, where at least one transmitter is not co-linear with the other two. At least one sensor is used to detect the sequences of radiation which are reflected from the scene. A round-trip propagation delay associated with each spatial point of interest in the scene being imaged is then calculated (step 420'), as described herein.

A reflective coefficient corresponding to each point of interest associated with the scene is then determined based on the sequence of radiation emitted by the transmitter, the reflected radiation detected by the sensors, and the calculated round-trip delays between the transmitter, the point of interest, and each sensor (step 430'). An image or representation of the scene is then generated based on the reflective coefficients (step 440), and the image or representation is then stored in a memory arrangement or displayed on a monitor or other display device.

The foregoing merely illustrates the principles of the invention. Various modifications and alterations to the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the invention. All patents and publications cited herein are incorporated herein by reference in their entireties.

What is claimed is:

1. A method for imaging a scene, the method comprising:
   sending a sequence of electromagnetic radiation from at least one transmitter;
   detecting reflections of the sequence from the scene using at least three sensors, wherein at least one sensor is not co-linear with the other sensors;
   calculating a reflectivity coefficient for each point of interest in the scene based on the detected reflections;
   generating a representation of the scene based on the reflective coefficients; and
   at least one of storing the representation in a memory arrangement or displaying the representation of the scene on a display device.

2. The method of claim 1, wherein the at least one transmitter comprises at least one of a laser or a light-emitting diode.

3. The method of claim 1, wherein the sequence of electromagnetic radiation comprises at least one of a pseudorandom number sequence, a modulated continuous wave, or a phase-modulated Fourier transformed pulse.

4. The method of claim 1, wherein calculating the reflectivity coefficient comprises determining a round-trip delay between each transmitter, the point of interest, and each sensor, and calculated the reflectivity coefficient based on the sequence of electromagnetic radiation, the amplitudes of the detected reflections for each sensor, and the round-trip delays.

5. The method of claim 4, wherein the reflectivity coefficients are calculated using a time-averaging technique to improve the spatial-temporal resolution.

6. The method of claim 1, further comprising:
   determining frequency changes between the sequence of electromagnetic radiation and the detected reflections; and
   determining a motion vector associated with each point of interest based on the frequency changes.

7. A method for imaging a scene, the method comprising:
   sending a distinct sequence of electromagnetic radiation from each of at least three transmitters, wherein at least one transmitter is not co-linear with the other transmitters;
   detecting reflections of the sequences from the scene using at least one sensor;
   calculating a reflectivity coefficient for each point of interest in the scene based on the detected reflections;
   generating a representation of the scene based on the reflective coefficients; and
   at least one of storing the representation in a memory arrangement or displaying the representation of the scene on a display device.

8. The method of claim 7, wherein each transmitter comprises at least one of a laser or a light-emitting diode.

9. The method of claim 7, wherein each sequence of electromagnetic radiation comprises at least one of a pseudorandom number sequence, a modulated continuous wave, or a phase-modulated Fourier transformed pulse.

10. The method of claim 7, wherein calculating the reflectivity coefficient comprises determining a round-trip delay between each transmitter, the point of interest, and each sensor, and calculated the reflectivity coefficient based on the sequences of electromagnetic radiation, the amplitudes of the detected reflections, and the round-trip delays.

11. The method of claim 10, wherein the reflectivity coefficients are calculated using a time-averaging technique to improve the spatial-temporal resolution.

12. The method of claim 7, further comprising:
determining frequency changes between the sequences of electromagnetic radiation and the detected reflections; and
determining a motion vector associated with each point of interest based on the frequency changes.

13. A system for imaging a scene, the system comprising:
at least one transmitter configured to send a sequence of electromagnetic radiation toward the scene;
at least three sensors configured to detect reflections of the sequence from the scene, wherein at least one sensor is not co-linear with the other sensors; and
a processing arrangement configured to:
(a) calculate a reflectivity coefficient for each point of interest in the scene based on the detected reflections;
(b) generate a representation of the scene based on the reflective coefficients; and
(c) at least one of store the representation in a memory arrangement or display the representation on a display device.

14. A system for imaging a scene, the system comprising:
at least three transmitters, wherein each transmitter is configured to send a distinct sequence of electromagnetic radiation toward the scene, and wherein at least one transmitter is not co-linear with the other transmitters;
at least one sensor configured to detect reflections of the sequences from the scene; and
a processing arrangement configured to:
(a) calculate a reflectivity coefficient for each point of interest in the scene based on the detected reflections;
(b) generate a representation of the scene based on the reflective coefficients; and
(c) at least one of store the representation in a memory arrangement or display the representation on a display device.

* * * * *